US012539226B2

(12) United States Patent
Torio

(10) Patent No.: US 12,539,226 B2

(45) Date of Patent: Feb. 3, 2026

(54) NAIL CORRECTING TOOL

(71) Applicant: Tadanaga Torio, Tokyo (JP)

(72) Inventor: Tadanaga Torio, Tokyo (JP)

( * ) Notice: Subject to any disclaimer, the term of this patent is extended or adjusted under 35 U.S.C. 154(b) by 251 days.

(21) Appl. No.: 18/252,791

(22) PCT Filed: Oct. 5, 2021

(86) PCT No.: PCT/JP2021/036839

§ 371 (c)(1),
(2) Date: May 12, 2023

(87) PCT Pub. No.: WO2022/102285

PCT Pub. Date: May 19, 2022

(65) Prior Publication Data

US 2024/0000599 A1 Jan. 4, 2024

(30) Foreign Application Priority Data

Nov. 12, 2020 (JP) ................................ 2020-188924

(51) Int. Cl.
*A61F 5/11* (2006.01)

(52) U.S. Cl.
CPC .................................... *A61F 5/11* (2013.01)

(58) Field of Classification Search
CPC .......... A61F 5/11; A61F 5/019; A61F 5/0111; A61F 5/0116; A61F 5/0585; A61F 13/063; A61F 13/064; A61F 13/06; A61F 5/0102
See application file for complete search history.

(56) References Cited

U.S. PATENT DOCUMENTS 1,785,376 A 12/1930 Buckner
2010/0160845 A1* 6/2010 Yoshikawa .............. A61F 5/11
602/31

FOREIGN PATENT DOCUMENTS

| | | | |
|---|---|---|---|
| JP | 2001-037535 | A | 2/2001 |
| JP | 2003-010218 | A | 1/2003 |
| JP | 2010-142588 | A | 7/2010 |
| JP | 2011-024776 | A | 2/2011 |
| JP | 2015-080703 | A | 4/2015 |
| KR | 10-2017-0092492 | A | 8/2017 |
| WO | 2022-102285 | A1 | 5/2022 |

OTHER PUBLICATIONS

Japan Patent Office, International Search Report and Written Opinion for PCT Application No. PCT/JP2021/036839. Mail date Dec. 14, 2021.
Japan Patent Office, Notification of Reasons for Refusal for Japanese Patent Application No. 2022-073246, mail date Oct. 14, 2025.

* cited by examiner

*Primary Examiner* — Ophelia A Hawthorne
(74) *Attorney, Agent, or Firm* — SoCal IP Law Group LLP; Mark Andrew Goldstein

(57) ABSTRACT

A nail correcting tool to effectively correct highly deformed nails is described herein. This nail correcting tool has a top surface and a bottom surface, and the bottom surface has a curved part and a straight part. In a state in which the end of the curved part is placed against the lateral edge of the nail, making the point of action to be said end, the fulcrum to be a point on the curved part away from said end, and the point of effort to be a point on the straight part, a force is applied to the point of effort and the lateral edge of the nail is thereby separated from the skin by the principle of leverage.

4 Claims, 14 Drawing Sheets

NAIL CORRECTING TOOL

RELATED APPLICATION INFORMATION

This patent claims priority from International PCT Patent Application No. PCT/JP2021/036839, filed Oct. 5, 2021 entitled, "NAIL CORRECTING TOOL", which claims priority to Japanese Patent Application No. 2020-188924, filed Nov. 12, 2020, all of which are incorporated herein by reference in their entirety.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

TECHNICAL FIELD

The present invention relates to a nail correcting tool.

BACKGROUND

Conventionally, as a nail correcting method, there is suggested a technique of attaching a small piece having a proper restoration force to the surface of a nail and gradually correcting a nail shape to a normal form, for example, Patent Document 1, Japanese Unexamined Patent Application, Publication No. 2001-37535

SUMMARY OF THE INVENTION

Problems to be Solved by the Invention

However, the conventional technique described in Patent Document 1 uses a restoration force of a small piece attached to a deformed nail to load the nail and correct a nail form. Such a method that uses the restoration force has a problem that a correcting effect cannot be obtained on a nail with a nail edge curled at a sharp angle, a nail deformed to bite into skin, or the like.

It is an object of the present invention, which has been made in view of such situations, to effectively correct highly deformed nails.

Means for Solving the Problems

To achieve the above object, a nail correcting tool according to one aspect of the present invention is a plate-shaped nail correcting tool having an abutting surface that is placed against a nail, the abutting surface including:

a straight part having a first length, and a curved part having a second length shorter than the first length and having a convex curvature on a side of the nail in contact with the abutting surface, the plate-shaped nail correcting tool including a first nail correcting function of, in a state in which an end of the curved part is placed against a lateral edge of the nail, with the end as a point of action, a point on the curved part away from the end as a fulcrum, and a point on the straight part as a point of effort, applying a force to the point of effort and thereby separating the lateral edge of the nail from skin by principle of leverage.

Effects of the Invention

According to the present invention, it is possible to effectively correct highly deformed nails.

DETAILED DESCRIPTION

Preferred Mode for Carrying Out the Invention

Hereinafter, embodiments of the present invention will be described with reference to the drawings.

Figure 1:
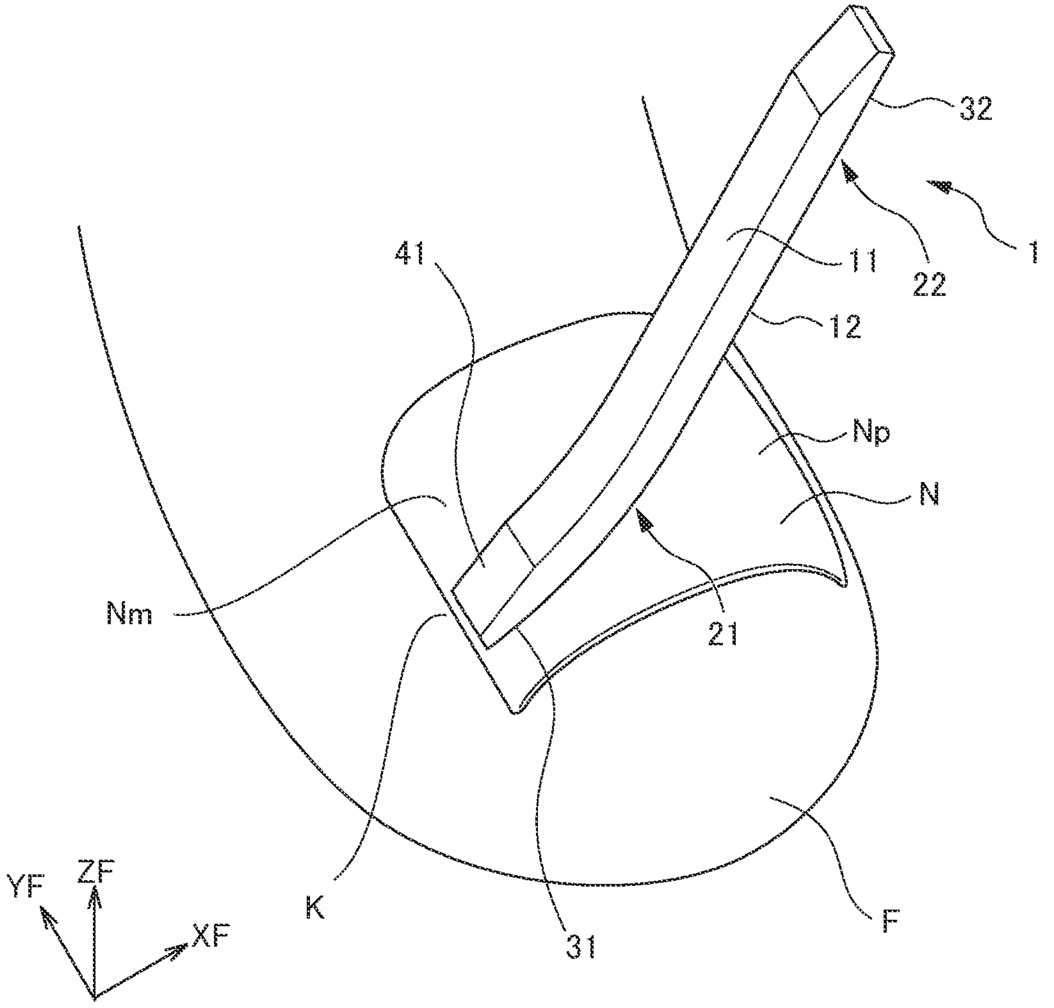
FIG. 1 is a perspective view of a nail correcting tool according to one embodiment of the nail correcting tool of the present invention.
Figure 2A:
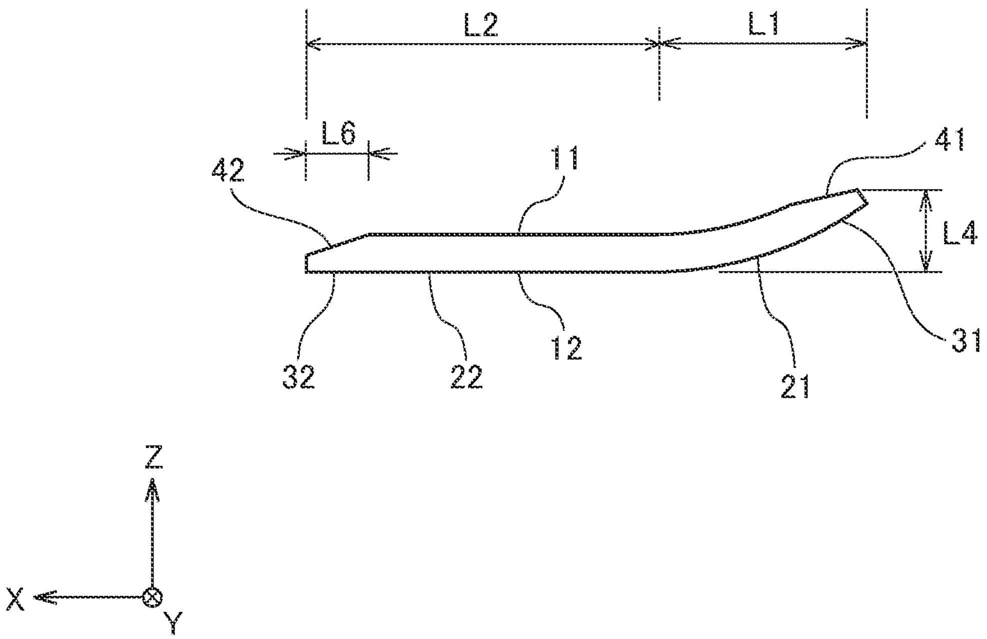
FIG. 2A is a side view of the nail correcting tool of FIG. 1.
Figure 2B:
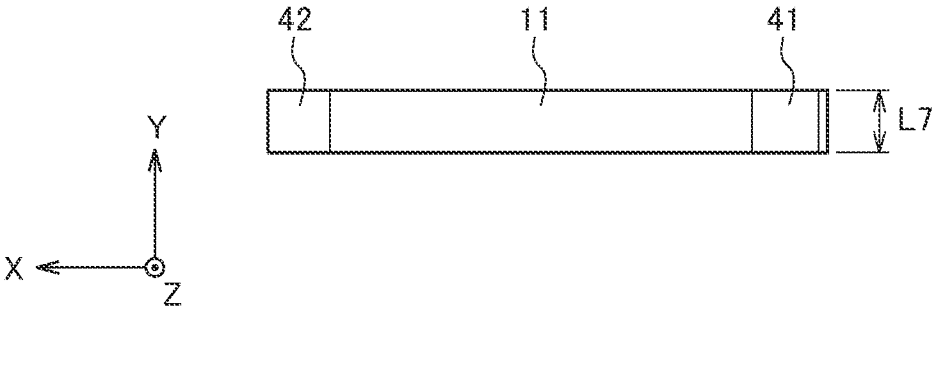
FIG. 2B is a top view of the nail correcting tool of FIG. 1.
Figure 3A:
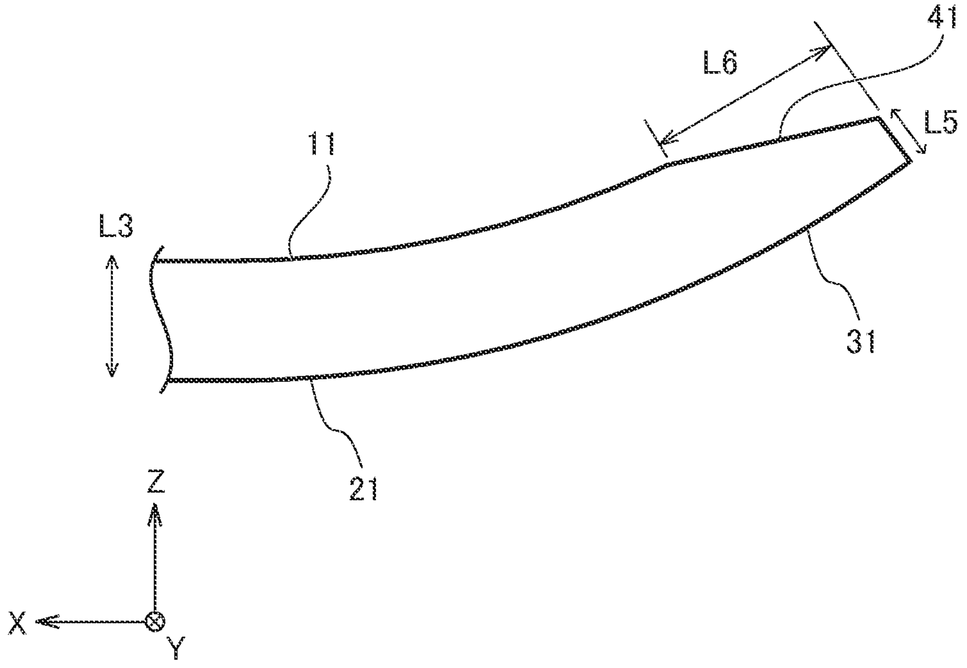
FIG. 3A is an image diagram shown by enlarged FIG. 2.
Figure 3B:
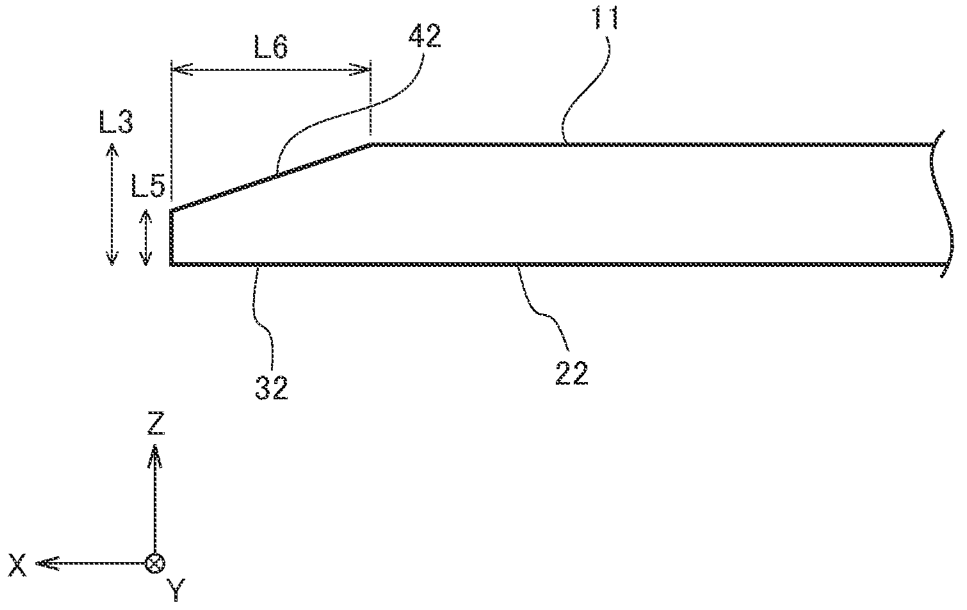
FIG. 3B is an image diagram shown by enlarged FIG. 2.

Referring to FIGS. 1 to 3, a configuration of a nail correcting tool 1 will be described. FIG. 1 is a perspective view of a nail correcting tool according to one embodiment of the nail correcting tool of the present invention. FIG. 2A is a side view of the nail correcting tool of FIG. 1. FIG. 2B is a top view of the nail correcting tool of FIG. 1. FIGS. 3A and 3B are image diagrams shown by enlarged FIG. 2.

Here, in the following description, unless otherwise specified, directions defined as follows shall be used.

Specifically, as a coordinate system based on a finger F, axes XF, YF, and ZF shown in FIG. 1 are used. That is, when assuming the finger F of a foot grounded on a floor, a surface having a direction in which gravity works (direction parallel to a ZF-axis) as shown in FIG. 1 as a normal, that is, the surface parallel to the axis XF and the axis YF is called "XF-YF plane". In the XF-YF plane, a surface which is placed against a pad of the finger F (corresponding to the floor described above) is called a "horizontal plane". In FIG. 1, the axis XF has a perpendicular relationship to the axis ZF and is also perpendicular to a direction in which a nail plate N extends. That is, a direction of an arrow of the axis XF shown in FIG. 1 is called a "positive direction of the axis XF", and the reverse direction is called a "negative direction of the axis XF". Also, in FIG. 1, the YF-axis has a perpendicular relationship to the axis ZF and is parallel to the direction in which the nail plate N extends. That is, a direction of the axis YF shown in FIG. 1 is called a "positive direction of the axis YF", and the reverse direction is called a "negative direction of the axis YF". Also, in FIG. 1, a direction of an arrow of the ZF-axis is called a "positive direction of the axis ZF", and the reverse direction is called a "negative direction of the axis ZF".

Further, as a coordinate system based on the nail correcting tool 1 according to one embodiment of the present invention, axes X, Y and Z shown in FIGS. 2A and 2B are used. Details will be described later, and as shown in FIGS. 2A and 2B, the nail correcting tool 1 has a rectangular shape having a long side and a short side and includes a structure of a curved plate member having a thickness smaller than the short side. That is, as shown in FIG. 2A, when a non-curved side of the plate member is grounded on the floor, a surface having a direction in which gravity works (direction parallel to the axis Z) shown in FIG. 2A as a normal, that is, the surface parallel to the axis X and axis Y is called an "X-Y plane". In FIG. 1, the axis X has a perpendicular relationship to the axis Z and is parallel to a long-side direction of the plate member. That is, a direction of an arrow of the axis X shown in FIG. 1 is called a "positive direction of the axis X", and the reverse direction is called a "negative direction of the axis X". Also, in FIG. 1, the Y-axis has a perpendicular relationship to the axis Z and is perpendicular to the long-side direction (parallel to a short-side direction). That is, a direction of the axis Y shown in FIG. 1 is called a "positive direction of the axis Y", and the reverse direction is called a "negative direction of the axis Y". Also, in FIG. 1, a direction of an arrow of the Z-axis shown in FIG. 1 is called a "positive direction of the axis Z", and the reverse direction is called a "negative direction of the axis Z.

The nail correcting tool 1 is a correcting tool used to correct the shape of the nail and includes a configuration of a rectangular plate member. A material of the nail correcting tool 1 is preferably a material having a restoration force (tensile force) while having hardness to such an extent that it does not break easily, having transparency, being highly workable, and having almost no effect on a body. As this material, for example, ABS resin is adopted in the present embodiment.

As shown in FIG. 1, the nail correcting tool 1 has a rectangular surface 11 and a surface 12 facing the surface 11. Here, as shown in FIG. 1, when viewed in the negative direction of the Z-axis (viewed from above) in a state where the pad of the finger F is placed on the horizontal plane, the surface 11 is located on an upper side, and the surface 12 is located to be placed against the nail plate N of the finger F. Therefore, hereinafter, the surface 11 is referred to as "the top surface 11", and the surface 12 is referred to as "the bottom surface 12". On the bottom surface 12, a part that is placed against the nail plate N is divided into a curved part 21 and a straight part 22.

As shown in FIG. 2A, the curved part 21 has a length L1 in a direction of the axis Z, and the straight part 22 has a length L2 in a direction of the axis X. As shown in FIG. 1, the curved part 21 and the straight part 22 are used to be placed against the nail plate N when the nail plate N is corrected. As will be specifically described later, when a lateral edge Nm is corrected as shown in FIG. 1, the curved part 21 is fixed to the lateral edge Nm. Then, with a position of the curved part 21 that is placed against the lateral edge Nm functioning as a point of action, a part of the straight part 22 functioning as a point of effort, and a predetermined position of the curved part 21 close to the point of action between the point of action and the point of effort functioning as a fulcrum, respectively, a constant force is applied to the point of action and the lateral edge Nm is thereby corrected by the principle of leverage. The force applied to the point of action in this way is hereinafter referred to as a "correction force". Therefore, the length L1 of the curved part 21 needs to be long enough to function as the fulcrum and the point of action respectively, when the curved part is placed against the nail plate N for the correction of the nail plate N. On the other hand, a part of the straight part 22 functions as the point of effort for the correction of the lateral edge Nm. Therefore, the length L2 of the straight part 22 needs to be long enough to such an extent that a practitioner manually applies, to the point of effort, a load required for the correction of the lateral edge Nm. Further, as will be described later, a portion of the straight part 22 that is not placed in contact is cut, and hence the length L2 needs to be determined in consideration of this cutting as well. In the present embodiment, the length L1 of 10 mm and the length L2 of 17 mm are adopted respectively.

As shown in FIGS. 3A and 3B, the curved part 21 and the straight part 22 have a thickness L3 in the Z-axis direction. In the present embodiment, a plurality of types of nail correcting tools 1 having different thicknesses L3 can be prepared to correspond to a thickness, hardness, and size of the nail plate N. Therefore, the practitioner can select the type of nail correcting tool 1 suitable for the thickness, hardness, and size of the nail plate N, to perform treatment. Specifically, for example, in the present embodiment, a first type of nail correcting tool 1 in which the thickness L3 of 1.8 mm is adopted and a second type of nail correcting tool 1 in which the thickness L3 of 1.1 mm is adopted are prepared. In this case, when the nail plate N is hard and thick, the first type of nail correcting tool 1 is selected. On the other hand, when the nail plate N has a general thickness or is thin, or for smaller nails other than a thumb nail, the second type of nail correcting tool 1 is selected.

Here, a reason the thickness L3 of 1.8 mm is adopted in the first type of nail correcting tool 1 is as follows. That is, if the thickness L3 is larger than 1.8 mm, the correction force applied to the nail plate N becomes excessively strong, and problems might occur that the nail plate N peels off from skin of the finger F and that the treatment is accompanied with severe pain. Further, if the thickness L3 is large, a problem occurs that labor is required for cutting the straight part 22. On the other hand, as the thickness L3 decreases, the correction force of the nail correcting tool 1 weakens. Therefore, the maximum thickness of 1.8 mm that does not cause the above-described problems is adopted as the thickness L3 of the first type of nail correcting tool 1 in the present embodiment.

Further, a reason the thickness L3 of 1.1 mm is adopted in the second type of nail correcting tool 1 is as follows. That is, if the thickness L3 is smaller than 1.1 mm, the correction force applied to the nail plate N excessively weakens, and a problem might occur that effect of correction is not obtained. On the other hand, as the thickness L3 increases, the correction force strengthens, but problems might occur that an originally thin nail plate N is damaged and that the treatment is accompanied with severe pain. Therefore, the maximum thickness of 1.1 mm that does not cause the above-described problems is adopted as the thickness L3 of the second type of nail correcting tool 1 in the present embodiment.

As described above, when the lateral edge Nm is corrected by the principle of leverage, a part of the curved part 21 functions as the fulcrum, and a position away from the fulcrum functions as the point of action. Therefore, when a degree of curving of the curved part 21 is excessively large, a surface which comes into contact with a part of the curved part 21 that functions as the point of action and the lateral edge Nm becomes small, and a large load is applied locally to this abutting surface. This might cause the problems that the nail correcting tool 1 peels off from the lateral edge Nm, the nail plate N peels off from the skin of the finger F and the treatment is accompanied with severe pain. Furthermore, as will be described later in detail, if the degree of curving of the curved part 21 is excessively large, a region of the curved part 21 that can function as the fulcrum is limited, and hence a problem that the treatment is hard to perform might occur. On the other hand, if the degree of curving of the curved part 21 is excessively small, the region that can function as the fulcrum widens, but the closer the curved part 21 is to a straight line, the harder the principle of leverage is to function. This might cause a problem that the correction force applied to the lateral edge Nm becomes smaller.

From the above, the degree of curving of the curved part 21 preferably secure a region such that the principle of leverage is to function and the end of the curved part can function as the fulcrum when the curved part 21 is placed against the lateral edge Nm. In the present embodiment, the curved part 21 is formed by bending the bottom surface 12 by a height L4 in the positive direction of the Z-axis from a state in which the straight part 22 is placed against the horizontal plane. Specifically, in the present embodiment, the height L4 of 1 mm is adopted.

As shown in FIG. 2, in the curved part 21, there is an end 31 on a side opposite to a side connected to the straight part 22. On the other hand, in the straight part 22, there is an end 32 on the side opposite to the side connected to the curved part 21. As shown in FIG. 3A, a gel spot 41 is provided on the top surface 11 facing the end 31 of the bottom surface 12. Further, as shown in FIG. 3B, a gel spot 42 is provided on the top surface 11 facing the end 32 of the bottom surface 12.

As shown in FIG. 3A, the gel spot 41 is formed by cutting the top surface 11 of the nail correcting tool 1 in a range of a length L6 from a distal end portion in the negative direction of the axis X so as to descend diagonally in a direction of the distal end portion. Then, the distal end portion is formed to have a thickness L5 as a thickness in the Z-axis direction. As shown in FIG. 3B, the gel spot 42 is formed by cutting the top surface 11 of the nail correcting tool 1 in a range of the length L6 from a distal end portion in the positive direction of the X-axis so as to descend diagonally in the direction of the distal end portion. Then, the distal end portion is formed to have the thickness L5 as the thickness in the Z-axis direction. Specifically, in the present embodiment, a size of 0.8 mm and a size of 3 mm are adopted as the thickness L5 and the length L6, respectively.

Here, a reason the size of 0.8 mm and the size of 3 mm are adopted as the thickness L5 and the length L6, respectively, is as follows.

That is, specifically, as will be described later with reference to FIG. 4, when the end 31 of the curved part 21 is placed against the lateral edge Nm and the lateral edge Nm is corrected by the principle of leverage, the end 31 and the gel spot 41 function as an adhesive applying surface. Further, when the end 32 of the straight part 22 is placed against the lateral edge Nm and the nail plate N is corrected, the end 32 and the gel spot 42 function as an adhesive applying surface. For this reason, the practitioner uses the gel spot 41 or 42 as an index to determine a position to which an adhesive is applied and an amount of adhesive applied. A length of 3 mm is adopted as the length L6 in the present embodiment that is a criterion for applying an appropriate amount of adhesive.

Specifically, as will be described later with reference to FIG. 4, for example, when the end 31 of the curved part 21 is placed against the lateral edge Nm and the lateral edge Nm is corrected by the principle of leverage, the adhesive is applied from the lateral edge Nm to the gel spot 41 in order to strengthen a fixing force of the end 31 and the lateral edge Nm. At this time, if the thickness L5 is excessively large (a height of the gel spot 41 is excessively large as viewed from the position of the lateral edge Nm), the adhesive cannot be continuously applied from the lateral edge Nm to the gel spot 41, which makes it difficult to strengthen the fixing force of the end 31 and the lateral edge Nm. On the other hand, if a large amount of adhesive is applied from a distal end of the lateral edge Nm to the gel spot 41 in order to strengthen the fixing force of the end 31 and the lateral edge Nm, problems might occur that labor is required in scraping off the adhesive adhered to the surface of the nail plate N after the nail correcting tool 1 is fixed, and that the adhesive adheres to skin. On the other hand, if the thickness L5 is excessively small (the height of the gel spot 41 is excessively small as viewed from the position of the lateral edge Nm), the adhesive can be easily applied, but resistance to deformation of the nail correcting tool 1 weakens, and hence the nail correcting tool 1 turns white to lose its function. Therefore, the thickness L5 of 0.8 mm is adopted in the present embodiment as the thickness that can facilitate the applying of the adhesive and secure a constant correction force.

Reasons the gel spot 41 and the gel spot 42 are cut and configured so as to descend diagonally in the direction of the distal end portion are as follows. Specifically, as will be described later with reference to FIG. 4, for example, when the end 31 of the curved part 21 is placed against the lateral edge Nm and the lateral edge Nm is corrected by the principle of leverage, the end 31 facing the gel spot 41 functions as the point of action. Therefore, if the gel spot 41 is cut and configured, for example, in a stepped manner instead of diagonally, a local force at the point of action is applied to a stepped portion, so that the stepped portion might turn white to lose its function, or the nail correcting tool 1 might be broken in the stepped portion. Therefore, the gel spot 41 and the gel spot 42 are cut and configured to descend diagonally to the distal end portion in order to maintain the resistance to deformation.

Since the nail correcting tool 1 has transparency, the practitioner can see at a glance the gel spot 41 configured on a top surface 11 side even when the end 31 is viewed from a bottom surface 12 side. Therefore, the practitioner can apply an appropriate amount of adhesive to an appropriate position at the end 31 while referring to the gel spot 41. Similarly, even when the end 32 is viewed from the bottom surface 12 side, the practitioner can see at a glance the gel spot 42 constituted on the top surface 11 side. Therefore, the practitioner can apply an appropriate amount of adhesive to an appropriate position at the end 32 while referring to the gel spot 42.

As shown in FIG. 2B, the nail correcting tool 1 has a width L7 as a length of the top surface 11 in the short-side direction. As described above with reference to FIG. 1, when the lateral edge Nm is corrected, the curved part 21 is fixed to the lateral edge Nm. Then, the lateral edge Nm is corrected by the principle of leverage. Therefore, the width L7 needs to be a width that is resistant to such an extent that even the nail correcting tool 1, to which a strong load is applied, cannot be easily broken. Specifically, for example, in the present embodiment, the width L7 of 3 mm is adopted. Here, a reason the width L7 of 3 mm is adopted is as follows. That is, when the width L7 is larger than 3 mm, an adhering area when the nail plate N and the bottom surface 12 are fixed is large, and a problem might occur that a range of damages on the nail plate N is extensive. Further, if the width L7 is large, a problem occurs that labor is required for cutting the straight part 22. On the other hand, as the width L7 decreases, the resistance to deformation of the nail correcting tool 1 weakens, whereby the nail correcting tool 1 turns white, to lose its function. The adhering area when the nail plate N and the bottom surface 12 are fixed becomes smaller, and hence a problem also occurs that the nail correcting tool 1 is easily detached from the nail plate N. Therefore, a maximum width of 3 mm that does not cause the above-described problems is adopted as the width L7 in the present embodiment.

The nail correcting tool 1 includes the rectangular top surface 11 and the bottom surface 12 as described above, and the bottom surface 12 is divided into the curved part 21 and the straight part 22 in the X-axis direction. Therefore, the treatment can be performed with the nail correcting tool 1 simply by changing an orientation of the nail correcting tool 1 in the X-axis direction, whether a correction target is, for example, a left foot, a right foot, the lateral edge Nm, or a lateral edge Np.

Next, with reference to FIG. 4, an operation of the nail correcting tool 1 having the configuration of FIGS. 1 to 3 described above will be described.

Prior to the description of the operation of the nail correcting tool 1, an adhesive for use in the treatment for the correction of the nail plate N will be described. As the adhesive, a light-curable adhesive is preferable. The reasons why the light-curable adhesive is preferable are as follows. That is, the light-curable adhesive has a high adhering force and can be cured by being irradiated with light, and hence, for example, unlike a type of adhesive that is cured by mixing first and second liquids, the light-curable adhesive can be gradually cured according to light irradiation time. Therefore, the practitioner can fix the nail correcting tool 1 to the nail plate N and proceed with the treatment while listening to a subject about a situation of pain felt when loading the nail plate N. Consequently, the pain felt by the subject can be suppressed. Further, the treatment can be interrupted and the adhesive can be reapplied, before completely fixing the nail correcting tool 1 to the nail plate N. In the present embodiment, two types of light-curable adhesives are used depending on its application. Specifically, as will be described later, a high-viscosity gel adhesive HV (hereinafter referred to as "gel HV") is for use in fixing the lateral edge Nm and the end 31, repairing a damaged portion of the nail plate N, or coating. A low-viscosity gel adhesive LV (hereinafter referred to as "gel LV") is for use in an application such as fixing of the lateral edge Nm and the end 31, repair when the nail plate N and the bottom surface 12 are about to peel off, filling of a gap between the nail plate N and the bottom surface 12, or coating.

Hereinafter, the operation of the nail correcting tool 1 will be described.

In step ST1, the practitioner applies the gel HV to the end 31 of the nail correcting tool 1. An amount of gel HV applied and a position to which the gel is applied are determined by the practitioner with reference to the gel spot 41. Specifically, when the practitioner sees the nail correcting tool 1 from the negative direction of the Z-axis (bottom surface 12 side) (in a top surface 11 direction), a region of the gel spot 41 can be visually recognized, and hence such an appropriate amount of adhesive as to be on the gel spot 41 can be applied to an appropriate location. As the amount of gel HV applied, an amount corresponding to ⅓ of a size of a rice grain is preferable.

In step ST2, the practitioner places the end 31, to which the gel HV is applied, against the lateral edge Nm, and brings the end 31 into close contact with the lateral edge Nm. At this time, if an excess gel HV is not removed, a portion of the nail plate N that is not suitable as a fulcrum is raised by the excess gel HV, and this raised portion becomes the fulcrum, whereby the lateral edge Nm cannot be effectively loaded. To solve the problem, the practitioner removes the gel HV protruding from between the end 31 and the lateral edge Nm with a spatula.

In step ST3, the practitioner irradiates the gel HV in a portion of the lateral edge Nm, against which the end 31 is placed, with ultraviolet rays (for example, ultraviolet rays with a wavelength of 365 n) by use of an LED lamp L (hereinafter referred to as "the lamp L"). Thereby, since the gel HV is cured, the end 31 and the lateral edge Nm are fixed.

In step ST4, the practitioner takes the gel HV at a tip of the spatula and applies the gel to a range from the distal end of the lateral edge Nm to a position of about ⅔ of the gel spot 41, in a state of step ST3 where the end 31 and the lateral edge Nm are fixed. When the amount of gel HV applied at this time is excessively large, the portion of the nail plate N that is not suitable as the fulcrum is raised by the excess gel HV, and this raised portion becomes the fulcrum, whereby the lateral edge Nm cannot be effectively loaded. On the other hand, when the amount of gel HV applied is excessively small, a problem occurs that the end 31 peels off from the lateral edge Nm or any correction force is not applied. The gel spot 41 can also solve such a problem. That is, the practitioner can apply the appropriate amount of adhesive for fixing, by referring to the region of the gel spot 41.

While holding a part of the straight part 22 of the nail correcting tool 1, the practitioner tries to tilt the straight part 22 in the negative direction of the Z-axis and confirms whether the lateral edge Nm and the end 31 are fixed, whether the lateral edge Nm is separated from skin K, and how much the lateral edge Nm is raised. Here, if it is confirmed that the lateral edge Nm is separated from the skin K, it can be seen that the end 31 acts as the point of action, a point on the curved part 21 acts as the fulcrum, a part of the straight part 22 acts as the point of effort and the lateral edge Nm can be corrected by the principle of leverage. Furthermore, depending on an amount of lateral edge Nm raised, it is possible to confirm adjustment of a positional relationship among the point of action, the fulcrum, and the point of effort. As a result of such confirmation, if it is expected that the lateral edge Nm can be sufficiently corrected, the process advances to step ST5. On the other hand, if the lateral edge Nm and the end 31 are not sufficiently fixed, if the lateral edge Nm is not separated from the skin K, or the like, that is, if it is not expected that the lateral edge Nm can be sufficiently corrected, the process may return to step ST3.

In step ST5, the practitioner further applies the gel HV between the bottom surface 12 and the nail plate N. The amount of gel HV is preferably such that the gel HV protrudes slightly from between the bottom surface 12 and the nail plate N when the straight part 22 is tilted toward the negative direction of the Z-axis. This is because a large amount of protruding gel HV causes a problem that labor is required for scraping off the surface of the nail plate N after the nail correcting tool 1 is fixed.

Figure 4:
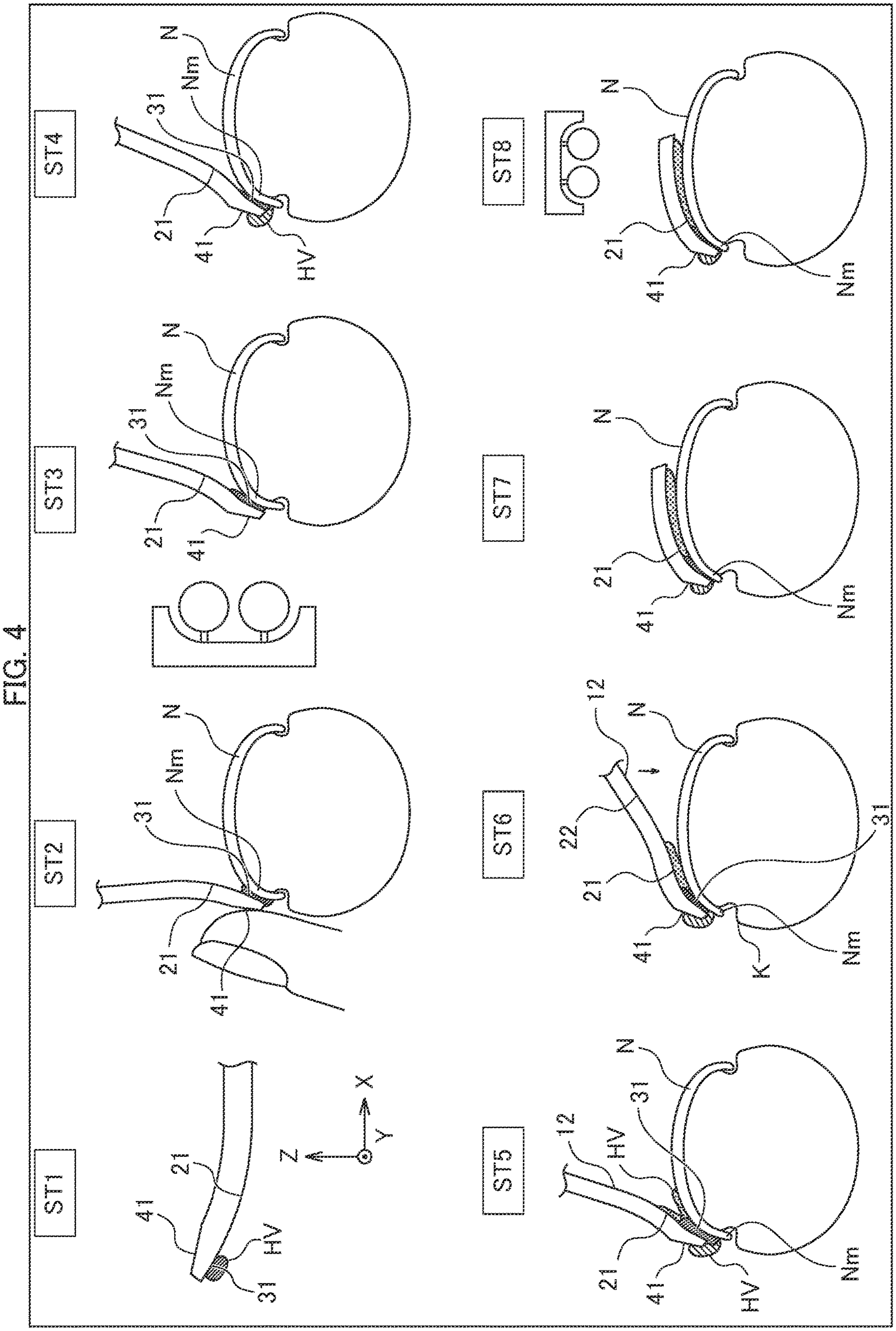
FIG. 4 is a view illustrating an operation of the nail correcting tool having a configuration of FIGS. 1 to 3.

In step ST6, the practitioner holds a part of the straight part 22 (the portion functioning as the point of effort) to tilt the part toward the negative direction of the Z-axis (an arrow direction in FIG. 4). Consequently, in the nail correcting tool 1, the end 31 of the curved part 21 functions as the point of action, the portion of the straight part 22 held by the practitioner functions as the point of effort, and a part of the curved part 21 that is close to the point of action between the point of action and the point of effort functions as the fulcrum, whereby the lateral edge Nm is separated from the skin K by the principle of leverage. Furthermore, the practitioner brings the bottom surface 12 from the curved part 21 to the portion of the straight part 22 close to the nail plate N. Here, based on a reference angle between the nail correcting tool 1 and the nail plate N immediately before step ST6, about a half of this reference angle is preferable as an angle at which the straight part 22 is tilted when bringing the bottom surface 12 close to the nail plate N. This is because when the straight part 22 is excessively (more than the half of a standard angle) tilted to be placed against the nail plate N, a problem might occur that the nail correcting tool 1 comes off from the nail plate N or the nail plate N peels off from the skin. After bringing the bottom surface 12 close to the nail plate N, the practitioner removes the gel HV protruding from between the bottom surface 12 and the nail plate N, with the spatula. The practitioner then fixes a position (the position where the bottom surface 12 is close to the nail plate N) when the nail correcting tool 1 is tilted toward the negative direction of the Z-axis, and in this state, the practitioner irradiates the gel HV at the position where the bottom surface 12 is brought close to the nail plate N with ultraviolet rays by use of the lamp L. Thereby, since the gel HV is cured, the bottom surface 12 and the nail plate N are fixed.

In step ST7, the practitioner cuts a portion of the straight part 22 that is not fixed to the nail plate N. Then, the practitioner scrapes off a cut cross section of the straight part 22 and its surrounding in a predetermined manner in order to arrange the nail correcting tool 1 and the nail plate N that are fixed to each other.

In step ST8, the practitioner applies the gel LV to fill a slight gap between the nail plate N and the nail correcting tool 1 that are fixed to each other. Then, the practitioner irradiates the applied gel LV with ultraviolet rays by use of the lamp L. Thereby, since the gel LV is cured, the nail correcting tool 1 is more firmly fixed to the nail plate N. Then, finally, the practitioner further applies a rice grain-sized amount of gel HV to the nail plate N as a whole. This can prevent the nail correcting tool 1 from being peeled from the nail plate N. Also, at this time, the practitioner applies the gel HV to a boundary between the nail plate N and cuticle of the finger F. This makes it possible to grasp how much a new nail has grown, so that the practitioner can check at a glance effect of the correction of the lateral edge Nm relative to an amount of nail grown.

In the description with reference to FIG. 4, it has been described that the curved part 21 of the nail correcting tool 1 is fixed to the lateral edge Nm and the lateral edge Nm is corrected by the principle of leverage, which is not limited. That is, in the nail correcting tool 1, the straight part 22 may be fixed to the lateral edge Nm and a shape of the nail plate N may be corrected. Therefore, with reference to FIGS. 5A to 5C, a part of the nail correcting tool that is applied to various nail shapes will be described.

Figure 5A:
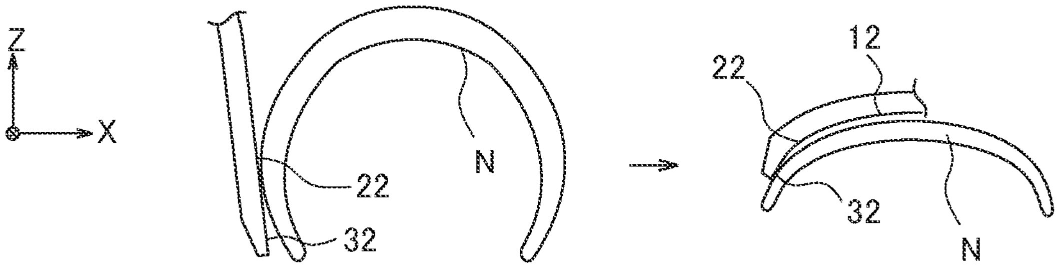
FIG. 5A is a view illustrating a part of the nail correcting tool applied to various nail shapes.
Figure 5B:
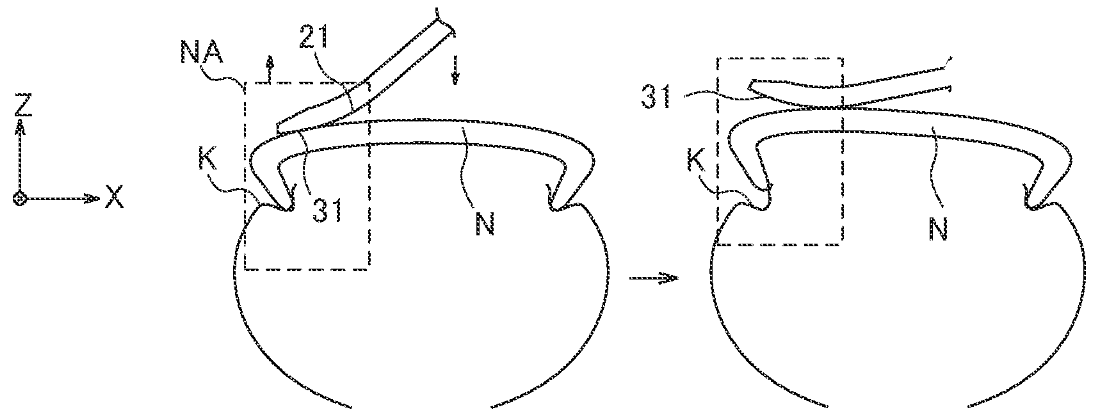
FIG. 5B is a view illustrating a part of the nail correcting tool applied to various nail shapes.
Figure 5C:
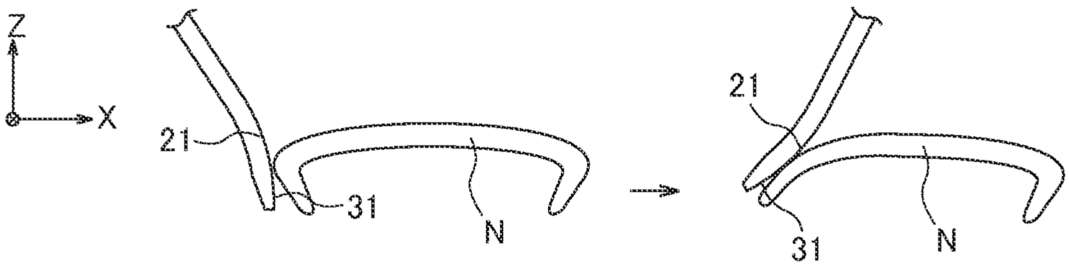
FIG. 5C is a view illustrating a part of the nail correcting tool applied to various nail shapes.

FIGS. 5A to 5C are views illustrating the part of the nail correcting tool that is applied to various nail shapes.

In general, it is considered that nails have a property of growing to be incurvated. It is normally considered that a force to spread the nail outward acts when external loads such as daily walking and exercise are added to a force to incurvate the nail and that the shape of the nail is maintained in a normal state by balance between the force to incurvate (inwardly working force) and the force to spread outward (outwardly working force). However, if such balance between the inwardly working force and the outwardly working force is lost, for example, when the inwardly working force becomes stronger than the outward spreading force, nail deformation might occur.

However, as for the deformation of the nail, its shape and degree of deformation vary. To effectively correct variously deformed nails, the nail correcting tool 1 of the present embodiment has a first nail correcting function (function in the curved part 21) of correcting the lateral edge Nm by the principle of leverage and additionally has a second nail correcting function (function in the straight part 22) by use of an elastoplastic force of a material of the nail correcting tool 1 itself.

Specifically, for example, as shown in FIG. 5A, the second nail correcting function is mainly exerted onto the nail plate N deformed to be entirely curved. That is, when correcting the nail plate N, the straight part 22 is fixed to the lateral edge Nm. Then, the bottom surface 12 is tilted toward the negative direction of the Z-axis and fixed to the nail plate N. In this case, the nail correcting tool 1 has a restoration force working due to properties of a material of the tool, and hence the nail correcting tool 1 curved to be placed against the nail plate N has the restoration force working in a direction of returning to a plate shape (positive direction of the Z-axis). That is, this restoration force acts as an outward spreading force onto the nail plate N deformed to be incurvated, and hence the shape of the nail plate N is corrected.

On the other hand, the first nail correcting function is mainly exerted onto the nail plate N with a part of the lateral edge Nm locally deformed as shown in FIGS. 5B and 5C.

FIG. 5B shows the nail plate N of a straight nail as a whole having a part of the lateral edge Nm that is locally deformed at a right angle or an acute angle and ingrown into the skin K (hereinafter referred to as an "ingrown nail"). In the case of this ingrown nail, since a part of the lateral edge Nm is ingrown into the skin K, it is difficult to place the nail correcting tool 1 against an ingrown portion. Therefore, such ingrown nails could not be effectively corrected by a conventional correcting technique. To solve this problem, the first nail correcting function is exerted to effectively correct the ingrown nail. That is, as shown in FIG. 5B, the end 31 of the curved part 21 is placed against and fixed to a predetermined position in the lateral edge Nm. Then, when the bottom surface 12 is tilted toward the negative direction of the Z-axis by the practitioner, as a result, the end 31 of the curved part 21 functions as the point of action, and a part of the curved part 21 functions as the fulcrum, to raise a portion included in a region NA shown in FIG. 5B in the positive direction of the Z-axis by the principle of leverage. As a result, the lateral edge Nm is separated from the skin K. Thus, the ingrown nail is effectively corrected by exerting the first nail correcting function.

Further, for example, as shown in FIG. 5C, the end 31 of the curved part 21 may be placed against a portion of the lateral edge Nm that is locally deformed at the right angle or the acute angle. Then, when the bottom surface 12 is tilted toward the negative direction of the Z-axis by the practitioner, as a result, the end 31 of the curved part 21 functions as the point of action, and a part of the curved part 21 functions as the fulcrum, to correct the deformed portion of the lateral edge Nm by the principle of leverage. Thus, the first nail correcting function is exerted while appropriately changing an abutting part of the nail correcting tool 1, whereby various deformed nails can be effectively corrected.

Thus, the nail correcting tool 1 has the first nail correcting function exerted by the curved part 21 and the second nail correcting function exerted by the straight part 22. Therefore, for example, even when the shape and degree of deformation are different between the lateral edge Nm and the lateral edge Np, the first and second nail correcting functions are combined and exerted, so that an effective treatment can be performed for each of the lateral edges Nm and Np.

Next, a relationship between an abutting position of the curved part 21 on the lateral edge Nm and the correction force will be described.

Figure 6A:
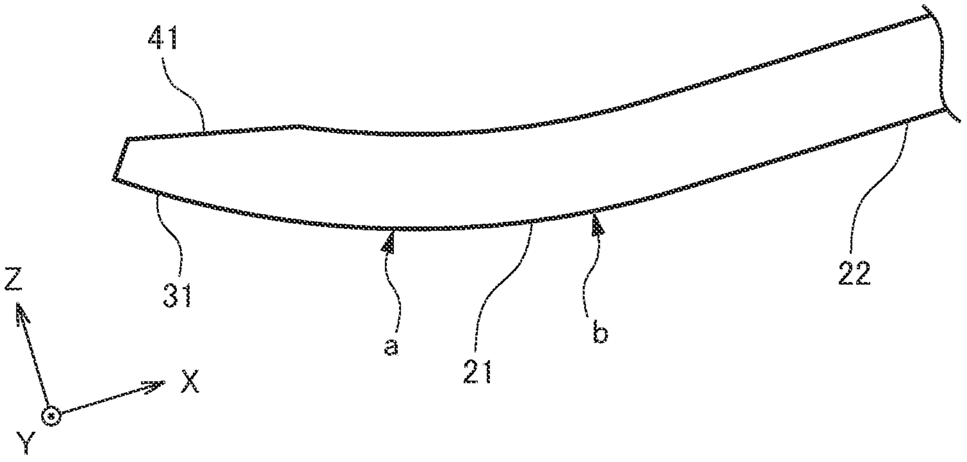
FIG. 6A is a view illustrating an abutting position of a lateral edge and a curved part.
Figure 6B:
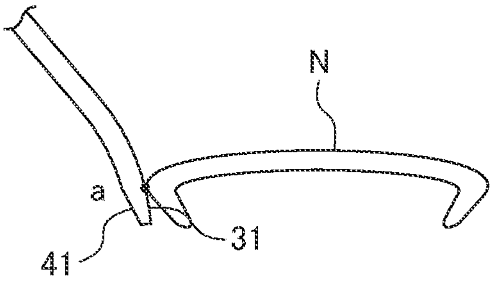
FIG. 6B is a view illustrating the abutting position of the lateral edge and the curved part.
Figure 6C:
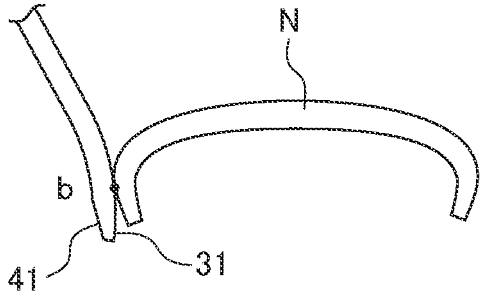
FIG. 6C is a view illustrating the abutting position of the lateral edge and the curved part.

FIGS. 6A to 6C are views illustrating the abutting position of the lateral edge and the curved part.

In general, the principle of leverage is established by balance between a value obtained by multiplying a distance from the fulcrum to the point of effort by a force applied to the point of effort and a value obtained by multiplying the distance from the fulcrum to the point of action and a force applied to the point of action. That is, for example, as shown in FIG. 6A, when the end 31 serves as the point of action at which the end 31 is placed against the lateral edge Nm, the distance from the point of action to the fulcrum differs depending on whether a point a or b is selected as the fulcrum. Therefore, each of the distance from the fulcrum to the point of effort, a force required at the point of effort and a force (correction force) applied to the point of action changes. Then, the practitioner can allow any position on the curved part 21 to function as the fulcrum so that effective correction can be performed depending on the thickness, hardness or size of the nail plate N, or the shape of the lateral edge Nm.

For example, when the end 31 is used as the point of action, a part of the straight part 22 is used as the point of effort and a force applied to the point of effort is made constant, in comparison of FIG. 6B with the point a as the fulcrum with FIG. 6C with the point b as the fulcrum, a larger force is applied to the point of action in FIG. 6B in which a distance from the point of action to the fulcrum is short. Therefore, for example, when the practitioner is to increase the correction force, it is more preferable to adopt the point a as the fulcrum. For example, when the nail plate N is small (the distance from the fulcrum to the point of action cannot be taken), the practitioner may adopt, as the fulcrum, the point a closer to the position (point of action) against which the end 31 is placed. That is, for example, when a larger load is to be applied to the point of action or when the width of the lateral edge Nm is small (the distance from the fulcrum to the point of action cannot be taken), the practitioner may adopt the point a as the fulcrum. On the other hand, for example, when the load applied to the point of action may be small or when the width of the lateral edge Nm is sufficiently large (the distance from the fulcrum to the point of action can be secured), the practitioner may adopt the point b as the fulcrum.

Thus, the curved part 21 can have the fulcrum at any position depending on the shape, hardness, and degree of deformation of the nail. Therefore, the practitioner can perform correction more effectively depending on practitioner's own treatment capability and the shape of the nail plate N.

Furthermore, since the nail correcting tool 1 is easy to process due to the properties of the material, the tool can be used by cutting a distal end of the end 31. The distance from the fulcrum to the point of action can be arbitrarily determined by using the curved part 21 in which the distal end of the end 31 is cut to an arbitrary length, and hence the practitioner can perform correction more effectively depending on the shape of the nail plate N. Further, the degree of curving of the curved part 21 can be arbitrarily selected by cutting the distal end of the end 31, and hence the practitioner can perform effective correction depending on various deformed nails.

Although one embodiment of the present invention has been described above, the present invention is not limited to the above-described embodiment, and modifications, improvements, and the like to the extent that the object of the present invention can be achieved are included in the present invention.

In the above-described embodiment, the bottom surface 12 of the nail correcting tool 1 is placed against the nail plate N to correct the nail plate N, but this is not limited. That is, the top surface 11 of the nail correcting tool 1 may be placed against the nail plate N to correct the nail plate N.

Figure 7A:
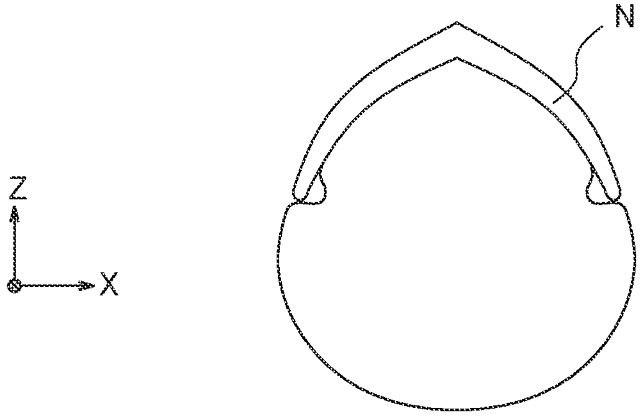
FIG. 7A is a view illustrating another example related to use of the nail correcting tool.
Figure 7B:
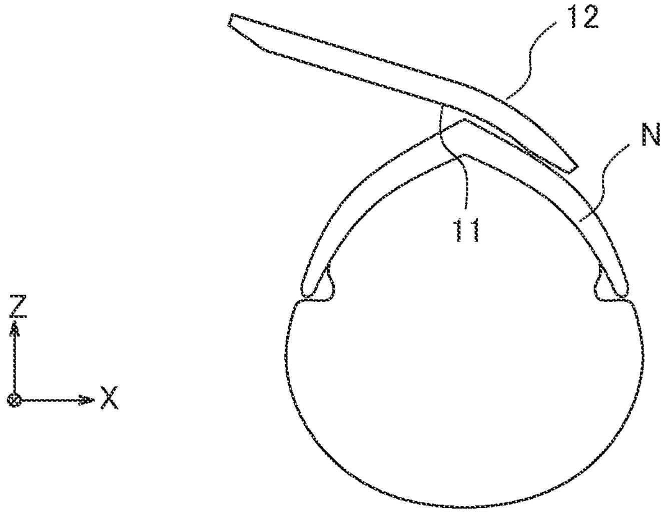
FIG. 7B is a view illustrating another example related to the use of the nail correcting tool.
Figure 7C:
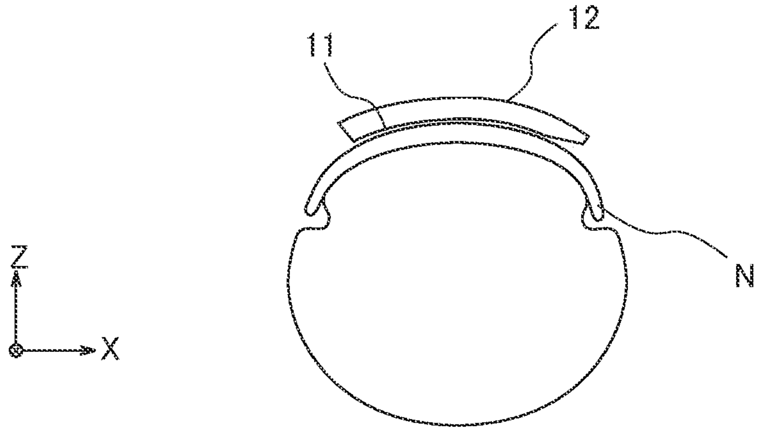
FIG. 7C is a view illustrating another example related to the use of the nail correcting tool.

FIGS. 7A to 7C are views illustrating another example related to the use of the nail correcting tool. Specifically, as shown in FIG. 7B, the top surface 11 side of the curved part 21 is placed against a nail (hereinafter referred to as a "triangular nail") deformed so that the nail plate N protrudes into a triangular shape in the positive direction of the Z-axis as shown in FIG. 7A. In this case, since the nail correcting tool 1 has the restoration force working due to the properties of the material, the nail correcting tool 1 curved to be placed against the nail plate N has the restoration force working in the direction of returning to the plate shape (positive direction of the Z-axis). That is, this restoration force acts onto the triangular nail as the outward spreading force, and hence the shape of the triangular nail is corrected. In this way, by placing a concave portion of the curved part 21 on the top surface 11 side against and in close contact with a convex shape of an upper part of the triangular nail, as shown in FIG. 7C, the triangular nail can be effectively corrected while preventing the nail correcting tool 1 from being peeled off.

As described above, the nail correcting tool 1 is easy to process due to the properties of the material and therefore can be used to correct broken nails and the like if cut to be small.

Figure 8A:
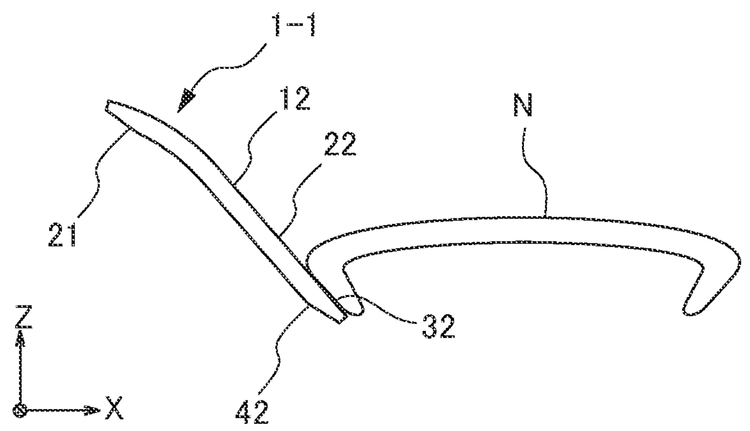
FIG. 8A is a view illustrating still another example different from FIG. 7 related to the use of the nail correcting tool.
Figure 8B:
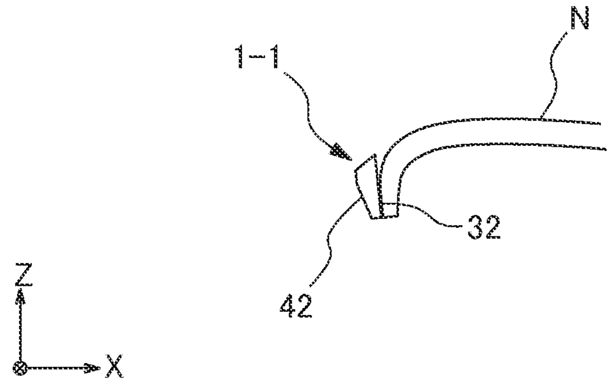
FIG. 8B is a view illustrating still another example different from FIG. 7 related to the use of the nail correcting tool.
Figure 8C:
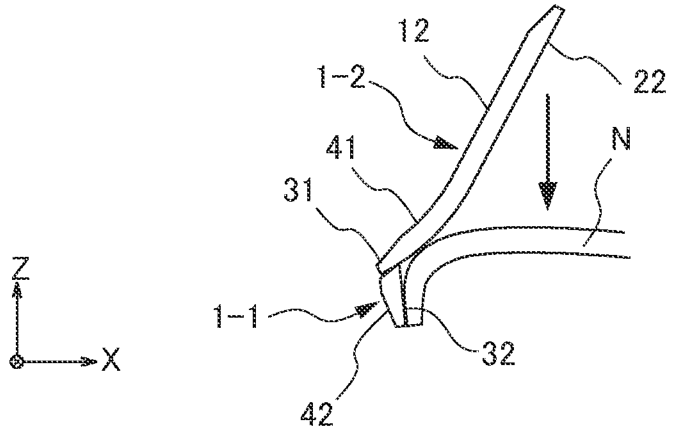
FIG. 8C is a view illustrating still another example different from FIG. 7 related to the use of the nail correcting tool.

Further, for example, the nail correcting tool 1 may be used in layers. Hereinafter, an example of a treatment performed using two nail correcting tools 1-1 and 1-2 will be described with reference to FIGS. 8A to 8C. FIGS. 8A to 8C are views illustrating still another example different from FIG. 7 related to the use of the nail correcting tool. Specifically, as shown in FIG. 8A, in a case of the nail plate N having the lateral edge Nm deformed at the right angle or the acute angle, first, an end 31 or an end 32 of the nail correcting tool 1-1 is placed against and fixed to the lateral edge Nm. Then, as shown in FIG. 8B, a straight part 22 of the nail correcting tool 1-1 is tilted until being substantially parallel to the Z-axis direction, and the nail correcting tool 1-1 is cut behind a fixed part, leaving only the fixed part. Furthermore, as shown in FIG. 8C, an end 31 of a curved part 21 of the other nail correcting tool 1-2 is placed against and fixed to the end 31 or 32 fixed to the lateral edge Nm, and the lateral edge Nm may be corrected by the principle of leverage. Thus, by overlapping and using the nail correcting tool 1-2 on the nail correcting tool 1-1, even highly deformed nails can be appropriately corrected. In the above description, to facilitate understanding, it has been described that the two nail correcting tools 1-1 and 1-2 are used. However, as described above, the nail correcting tool 1 includes both the curved part 21 and the straight part 22. Therefore, the practitioner may use the straight part 22 of the nail correcting tool 1-1 as the nail correcting tool 1-1 in FIG. 8C, and the curved part 21 of the cut nail correcting tool 1-1 as the nail correcting tool 1-2 in FIG. 8C. This enables the treatment described with reference to FIGS. 8A to 8C, only with one nail correcting tool 1.

Figure 9:
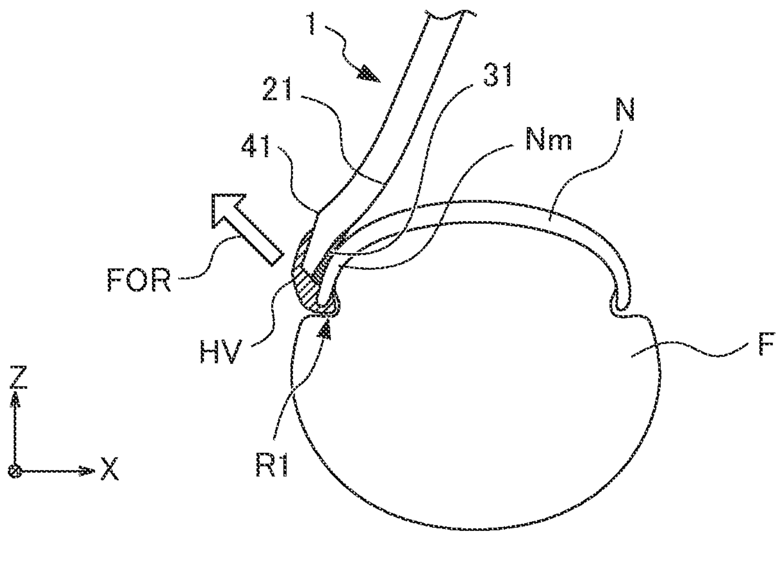
FIG. 9 is a view illustrating a further example different from FIGS. 7 and 8 related to the use of the nail correcting tool.

For example, the nail correcting tool 1 can also be used by an adhering method as follows. FIG. 9 is a view illustrating a further example different from FIGS. 7 and 8 related to the use of the nail correcting tool. In the adhering method in the example of FIG. 9, gel HV is applied at a different position from that in step ST4 of FIG. 4. That is, in the example of FIG. 9, the gel HV is also applied to a region R1 between a nail plate N and a finger F. Then, the gel HV applied in this way is irradiated with ultraviolet rays by use of a lamp L, thereby curing the gel HV. Thereafter, when the practitioner tilts the correcting tool 1 as shown in step ST6 of FIG. 4, a force is exerted in a direction shown with an arrow FOR in FIG. 9 (hereinafter referred to as “force FOR”) to separate the nail correcting tool 1 from the nail plate N.

Here, when the gel HV is applied as shown in step ST4 of FIG. 4, the gel HV is fixed due to adhering to the surface of the nail plate N. In contrast, when the gel HV is applied as shown in FIG. 9, the gel HV is cured integrally from above a gel spot 41 of the correcting tool 1 (a position in the positive direction of the axis Z and the negative direction of the axis X) to the region R1. Due to such a shape of the cured gel HV, the tool is fixed to support the nail plate N. Consequently, the correcting tool 1 and the nail plate N are fixed more firmly than in FIG. 4 and the like, and this fixed state is maintained even when the practitioner tilts the nail correcting tool 1 as in step ST6 of FIG. 4. That is, when the practitioner judges that the gel HV can be applied also to the region R1 between the nail plate N and the finger F, applying the gel HV as shown in FIG. 9 can more firmly fix the nail correcting tool 1 and the nail plate N. This makes it possible to effectively correct highly deformed nails.

Furthermore, the practitioner can apply the method of applying the gel HV described with reference to FIG. 9 to the nail plate N of the example described with reference to FIGS. 8A to 8C. Specifically, for example, the practitioner can apply the gel HV as shown in FIG. 9 and then cure the gel by use of the lamp L, without using the nail correcting tool 1-1 shown in FIG. 8C.

Figure 10:
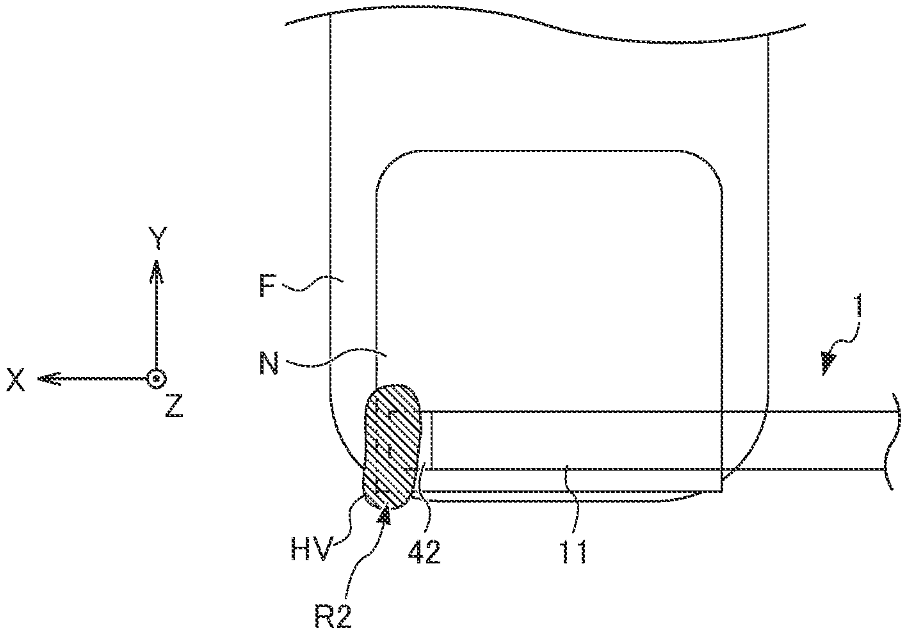
FIG. 10 is a view illustrating a further example different from FIGS. 7 to 9 related to the use of the nail correcting tool.

FIG. 10 is a view illustrating a further example that is different from FIGS. 7 to 9 related to the use of the nail correcting tool. In the adhering method of the example of FIG. 10, gel HV is applied at a different position from that in FIG. 5B. In the example of FIG. 9, the gel HV is applied to the region R1 between the nail plate N and the finger F via the positive direction of the axis X, and the practitioner may apply the gel HV as shown in FIG. 10. That is, the practitioner can apply the gel HV to a region between a nail plate N and a finger F via a region R2 in the negative direction of the axis YF, as shown in the example of FIG. 10. Specifically, in the example of FIG. 10, as described above, the gel HV is applied in the positive direction of the axis X as viewed from the nail correcting tool 1, and is also applied to the region R2 in the negative direction of the axis Y. Although not shown, the gel HV is also applied to the region between the nail plate N and the finger F via a position of the region R2 in the negative position of the axis Z. Then, the gel HV applied in this way is irradiated with ultraviolet rays by use of the lamp L, thereby curing the gel HV.

Thereby, as described with reference to FIG. 9, due to a shape of the cured gel HV, the tool is fixed to support the nail plate N. Consequently, the correcting tool 1 and the nail plate N are fixed more firmly than in FIG. 4 and the like, and this fixed state is maintained also when the practitioner tilts the nail correcting tool 1 as shown in step ST6 of FIG. 4. That is, when the practitioner judges that the gel HV can also be applied to the region R1 between the nail plate N and the finger F, applying the gel HV as shown in FIG. 10 can more firmly fix the nail correcting tool 1 and the nail plate N. This makes it possible to effectively correct highly deformed nails.

When the practitioner judges that the gel HV cannot be applied to the region R1 between the nail plate N and the finger F and the region R2 of the nail plate N in the negative direction of the axis Y described with reference to FIGS. 9 and 10 and the like, the gel HV may be applied as in step ST4 of FIG. 4. Specifically, for example, if the nail plate N is submerged in the finger F, such a method of applying the gel HV as shown in FIG. 9 is not adopted, and the applying method at step ST4 shown in FIG. 4 is preferably adopted. For example, when the nail plate N is short with respect to the finger F (state close to a so-called deep nail), it is preferable not to adopt such a method of applying the gel HV as shown in FIG. 10.

Here, in the example of FIG. 5A described above, by use of the nail correcting tool 1, not only the nail plate N but also the nail correcting tool 1 itself are deformed. Also, in the above description of FIG. 5B, the end of the nail plate N is raised using the nail correcting tool 1. Further, in the example of FIG. 5C described above, the nail correcting tool 1 is (comparatively) not deformed, and the nail plate N is deformed. Thus, whether or not the nail plate N is deformed depends on balance between restoration force of the nail plate N and the restoration force of the nail correcting tool 1. Here, when the thickness L3 of the nail correcting tool 1 varies, the restoration force of the nail correcting tool 1 varies. Therefore, as described above, a plurality of types of nail correcting tools 1 having different thicknesses L3 are prepared.

Figure 11:
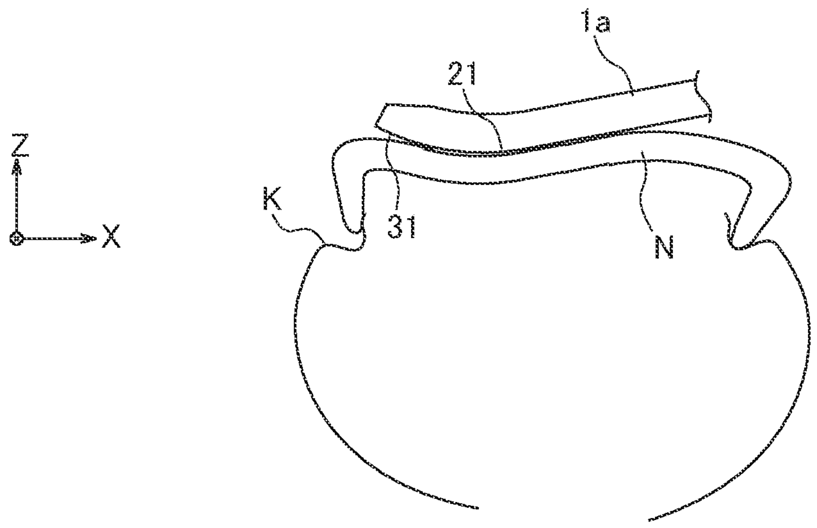
FIG. 11 is a view illustrating a further example different from FIGS. 7 to 10 related to the use of the nail correcting tool.

FIG. 11 is a view illustrating a further example different from FIGS. 7 to 10 related to the use of the nail correcting tool. That is, the example of FIG. 11 shows an example of correction by use of a nail correcting tool 1*a* having a large thickness and providing a high restoration force among the nail correcting tools of the present embodiment. Specifically, the example of the correction shown in FIG. 11 shows an example where the nail of the example of FIG. 5B described above is corrected using the nail correcting tool 1*a* providing a higher restoration force due to a larger thickness L3. In the example of FIG. 11, the nail correcting tool la is not deformed because the thickness L3 is large. Then, a nail plate N is firmly fixed to an end 31 of a curved part 21 of the nail correcting tool 1*a* with an unshown gel. Then, as shown on the left side of FIG. 5B, the nail correcting tool 1*a* on a positive direction side of the axis X is pressed down in the negative direction of the axis Z. Consequently, the nail plate N is deformed from the shape shown in FIG. 5B, as shown in FIG. 11. Thus, the nail correcting tool of the present embodiment can deform the nail plate N during treatment, when the gel is applied and fixed to the nail plate N only in the positive direction of the axis ZF.

Conventional correcting tools originally aim to promote deformation of the nail plate N by performing a number of treatments over a long time. Furthermore, some of the tools do not deform the nail plate due to small restoration force despite taking a long time and are less effective.

In contrast, the nail correcting tool 1 of the present embodiment has a high restoration force and can relieve pain or the like, by deforming the ingrown nail in one treatment to obtain a state where the nail plate N does not bite into the finger F. Furthermore, since the nail correcting tool 1 and the nail plate N are fixed using the gel, the tool can be applied to nails having a shape that is difficult to conventionally treat. The nail correcting tool 1*a* having the large thickness L3 has been described with reference to the example of FIG. 11 and as compared with the nail correcting tool 1 in the example of FIG. 5B and can be applied also to the other nail shapes described above. That is, the practitioner can change an amount of deformation of the nail plate N by using the nail correcting tool 1 having a different thickness L3 as appropriate depending on each nail shape.

Furthermore, the nail correcting tool 1 of the present embodiment is useful not only for various nail shapes described above but also for a shape of a nail that is not an incurvated nail but is an ingrown nail and also a deep nail. Although not shown, characteristics of the nail having the shape of the nail that is not the incurvated nail but is the ingrown nail and also the deep nail will be described using a coordinate system based on the finger F shown in FIG. 1. This nail is the deep nail and is therefore short in the direction of the axis YF. Also, the ingrown nail that is not the incurvated nail is less curved in the direction of the axis ZF. Consequently, an edge of the nail in the direction of the axis XF is ingrown shallowly with respect to the finger F in a direction substantially parallel to the XF-YF plane. In consequence, flesh of the finger F rides on the nail plate N in the positive direction of the axis ZF. Thereby, when the axis ZF is viewed from the positive direction, a length of the nail plate N in the direction of the axis ZF is shortened by the ridden flesh. Thus, a nail having a shape that is not an incurvated nail but is an ingrown nail as well as a deep nail is short in both the direction of the axis XF and the direction of the axis YF. That is, the nail has a small area when viewed from the positive direction of the axis ZF.

For this nail, it is difficult to apply the conventional nail correcting tool. That is, it is difficult to apply the conventional correcting tool that performs some kind of fixing to an extended portion of the nail. For example, the conventional correcting tool with a small restoration force may not make correction without exerting a sufficient force even if applied because the length of the tool in the direction of the axis XF is short. However, the nail correcting tool 1 of the present embodiment has a high restoration force and the curved part 21 and can therefore exert a force for correcting even a nail having a narrow area. Specifically, the nail correcting tool 1 of the present embodiment can make appropriate correction even for a highly deformed nail such as a nail having a shape that is not an incurvated nail but is an ingrown nail as well as a deep nail.

Figure 12:
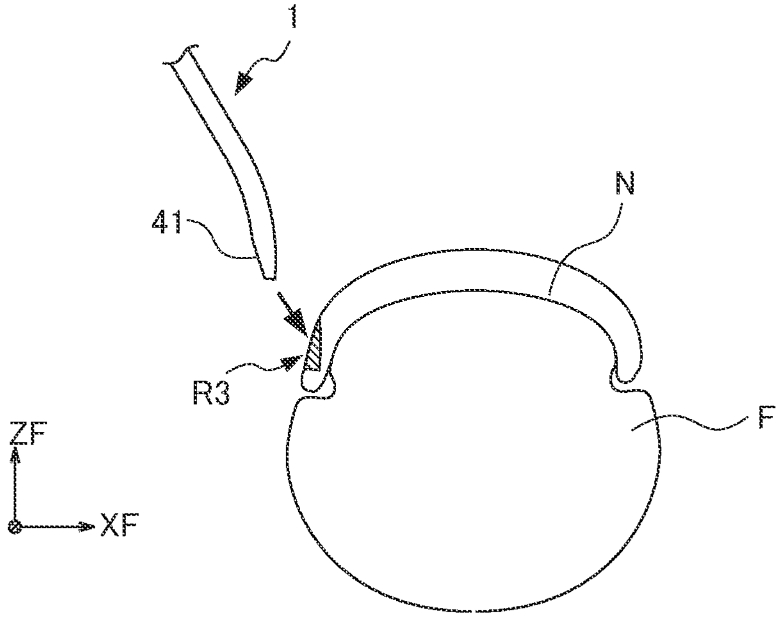
FIG. 12 is a view illustrating a still further example different from FIGS. 7 to 11 related to the use of the nail correcting tool.

Further, in the above-described embodiment, it has been described that the practitioner fixes the nail correcting tool 1 to the surface of the nail plate N or the like by applying the gel, but the tool may be fixed as follows. FIG. 12 is a view illustrating a still further example different from FIGS. 7 to 11 related to the use of the nail correcting tool. That is, as shown in FIG. 12, the practitioner can scrape off a part of a thick nail plate N and fix a nail correcting tool 1 by use of a gel with the tool fitted into a scraped space. Specifically, first, the practitioner scrapes off a region R3 from the nail plate N of FIG. 12. Then, the practitioner applies the gel into the region R3 and cures the gel by use of a lamp L with the nail correcting tool 1 fitted as shown with an arrow. Thereby, the nail correcting tool 1 and the nail plate N are more firmly fixed.

That is, by fitting the nail correcting tool 1 into the scraped region R3, an area in contact with the nail correcting tool 1 and the nail plate N can be increased. This can make the fixing more firmly. Further, although not shown, when the gel is applied to a gel spot 41 of the nail correcting tool 1 fitted in the region R3 in the negative direction of the axis XF, the gel is integrally cured (in a state where a structure in the axis XF direction is small), thereby making the fixing more firmly.

In the above-described embodiment, the practitioner judges the position to which the adhesive is applied and the amount of adhesive applied using the gel spots 41 and 42 as indices. Further, it has been described that the length of 3 mm is adopted as the length L6 in the present embodiment that is the criterion for applying the appropriate amount of adhesive, but the amount of gel applied is not limited to this example. That is, for example, it is sufficient for the practitioner to adjust the amount of gel applied using the gel spots 41 and 42 as the indices.

Specifically, for example, the practitioner is assumed to judge that the fixing of the nail correcting tool 1 may be limited to some extent to be easy to peel off for re-correction, based on the shape of the nail plate N and history of previous correction. In this case, the practitioner can apply a gel to a region of the gel spot 41 with a predetermined proportion (for example, 20%) and fix the tool. For example, the practitioner is assumed to judge that it is necessary to firmly fix the nail correcting tool 1, based on the shape of the nail plate N and the history of the previous correction. In this case, the practitioner can apply the gel to a region of the gel spot 41 as a whole (i.e., 100%) and fix the tool. Furthermore, as described above with reference to FIGS. 9 and 10, the gel spot 41 is used as the index, and the gel is applied to a side which does not come into contact with the nail plate N and the nail correcting tool 1 (region R1 in FIG. 9) and also to the region R2 in the negative direction of the axis YF where the nail plate N is extended and applied to all sides as much as possible, so that the tool can be fixed more firmly. Thus, the gel spots 41 and 42 are indices for the practitioner to grasp the amount of gel applied and the applying position and can improve convenience in treatment.

In summary, in the case of using the nail correcting tool 1 of the present embodiment, the gel HV cured with ultraviolet rays from the lamp L is used, and hence the nail correcting tool 1 can be freely fixed depending on the practitioner's judgment, that is, the state of the nail plate N. The nail correcting tool 1 of the present embodiment has the gel spots 41 and 42 and the like and can therefore improve convenience in using the gel HV.

In the above-described embodiment, the lateral edge Nm is corrected using one nail correcting tool 1, but this is not limited. That is, for example, the one nail correcting tool 1 may be placed against the lateral edges Nm and Np and may simultaneously correct the lateral edges Nm and Np.

In the above-described embodiment, the gel HV is used when placing the end 31 against the lateral edge Nm, but this is not particularly limited, and the gel LV may be used when placing the end 31 against the lateral edge Nm.

In summary, the nail correcting tool 1 to which the present invention is applied is sufficient when it is as follows and can take various embodiments.

That is, the nail correcting tool to which the present invention is applied is a plate-shaped nail correcting tool having an abutting surface (the bottom surface 12) that is placed against a nail (the nail plate N), the abutting surface including:

a straight part (the straight part 22) having a first length (length L2 in FIG. 2), and a curved part (the curved part 21) having a second length (the length L1 in FIG. 2) shorter than the first length and having a convex curvature on a side of the nail in contact with the abutting surface, the nail correcting tool including a first nail correcting function (for example, the first nail correcting function in FIGS. 5B and 5C) of, in a state in which an end of the curved part is placed against a lateral edge of the nail, with the end as a point of action, a point on the curved part away from the end as a fulcrum, and a point on the straight part as a point of effort, applying a force to the point of effort and thereby separating the lateral edge of the nail from skin by principle of leverage.

Thereby, an appropriate load can be applied to the shape (for example, the lateral edge Nm in FIGS. 5B and 5C) of the deformed nail that cannot be corrected by a correcting method using an elastoplastic force (restoration force of the material) of the nail correcting tool, and hence the shape can be effectively corrected.

Also, the nail correcting tool further includes:

a second nail correcting function (for example, the second nail correcting function in FIG. 5A) of separating the lateral edge of the nail from the skin by use of an elastoplastic force by placing at least a part of the straight part against the nail including the lateral edge.

Thereby, for example, an appropriate load can be applied to a nail plate as a whole deformed into a curved state, and hence the shape can be effectively corrected.

Further, in the nail correcting tool, the curved part of the abutting surface and the straight part include, at respective ends, index portions (the gel spots 41 and 42) that serve as indices of a location to which an adhesive adheres for placing the nail correcting tool against the nail including the lateral edge.

Thereby, an appropriate amount of adhesive for fixing the nail correcting tool to the nail plate can be applied at an appropriate position, and hence it is possible to prevent the nail correcting tool from being peeled off or the lateral edge from being raised during the correcting.

Furthermore, the curved part has a region that serves as the fulcrum in the first nail correcting function.

Thereby, nails having various shapes (for example, nails shown in FIGS. 6B and 6C) can be appropriately corrected.

EXPLANATION OF REFERENCE NUMERALS

1 . . . nail correcting tool, 11 . . . top surface, 12 . . . bottom surface, 21 . . . curved part, 22 . . . straight part, 31, 32 . . . end, 41, 42 . . . gel spot

The invention claimed is:

1. A plate-shaped nail correcting tool having an abutting surface configured to be placed against a nail, the abutting surface including:

a straight part having a first length, and a curved part having a second length shorter than the first length and having a convex curvature on a side of the nail in contact with the abutting surface, the plate-shaped nail correcting tool comprising a first nail correcting function in a state in which an end of the curved part on a side opposite to a side connected to the straight part is configured to be placed against a lateral edge of the nail, with the end as a point of action, a point on the curved part away from the end as a fulcrum, and a point on the straight part as a point of effort;

wherein applying a force to the point of effort thereby separates the lateral edge of the nail from skin by principle of leverage.

2. The plate-shaped nail correcting tool according to claim 1, further comprising:

a second nail correcting function configured to separate the lateral edge of the nail from the skin by use of an elastoplastic force by placing at least a part of the straight part against the nail including the lateral edge.

3. The plate-shaped nail correcting tool according to claim 2, wherein the curved part of the abutting surface and the straight part include, at respective ends, index portions that serve as indices of a location to which an adhesive adheres for placing the plate-shaped nail correcting tool against the nail including the lateral edge.

4. The plate-shaped nail correcting tool according to claim 1, wherein the curved part has a region that serves as the fulcrum in the first nail correcting function.

* * * * *